(12) United States Patent
Lai et al.

(10) Patent No.: US 9,837,244 B2
(45) Date of Patent: Dec. 5, 2017

(54) SAMPLE HOLDING DEVICE FOR STUDYING LIGHT-DRIVEN REACTIONS AND SAMPLE ANALYSIS METHOD USING THE SAME

(71) Applicant: Industrial Technology Research Institute, Hsin-Chu (TW)

(72) Inventors: Ming-Wei Lai, Taichung (TW); Shen-Chuan Lo, Hsinchu (TW)

(73) Assignee: INDUSTRIAL TECHNOLOGY RESEARCH INSITUTE, Hsin-Chu (TW)

( * ) Notice: Subject to any disclaimer, the term of this patent is extended or adjusted under 35 U.S.C. 154(b) by 223 days.

(21) Appl. No.: 14/583,442

(22) Filed: Dec. 26, 2014

(65) Prior Publication Data

US 2016/0189918 A1 Jun. 30, 2016

(51) Int. Cl.
*H01J 37/22* (2006.01)
*F21L 4/04* (2006.01)
(Continued)

(52) U.S. Cl.
CPC ............. *H01J 37/20* (2013.01); *F21L 4/04* (2013.01); *H01J 37/226* (2013.01);
(Continued)

(58) Field of Classification Search
CPC ...................................................... H01J 37/20
See application file for complete search history.

(56) References Cited

U.S. PATENT DOCUMENTS 5,124,645 A 6/1992 Rhoden et al.
7,291,847 B2 11/2007 Morrison
(Continued)

FOREIGN PATENT DOCUMENTS

CN 102820196 12/2012
CN 103344617 A 10/2013
(Continued)

OTHER PUBLICATIONS

F Cavalca et al., "In situ transmission electron microscopy of light-induced photocatalytic reactions," 2012 Nanotechnology 23:7 Feb. 24, 2012 p. 075705.
(Continued)

*Primary Examiner* — David E Smith
*Assistant Examiner* — James Choi
(74) *Attorney, Agent, or Firm* — WPAT, PC (57) ABSTRACT

A sample holding device for studying light-driven reactions and a sample analysis method using the same are disclosed. The sample holding device comprises a main body, a supporting structure and a light source assembly. The main body has a channel which has a first end and a second end opposite to the first end, and a focusing lens which is located on the second end. The supporting structure is located on one end of the main body for sample supporting. The light source assembly is detachably disposed on the other end opposite to the end which is disposed with the supporting structure. The light source assembly emits a light beam into the first end of the channel. The light beam then irradiates the sample which locates on the supporting structure after passing through the focusing lens.

12 Claims, 7 Drawing Sheets

(51) Int. Cl.
  H01J 37/20    (2006.01)
  H01J 37/26    (2006.01)
  G01N 23/20    (2006.01)
  H01R 13/62    (2006.01)
(52) U.S. Cl.
  CPC ............ *H01J 37/228* (2013.01); *H01J 37/26* (2013.01); *G01N 23/20025* (2013.01); *G01N 2223/307* (2013.01); *H01J 2237/206* (2013.01); *H01J 2237/20207* (2013.01); *H01R 13/6205* (2013.01)

(56) References Cited

U.S. PATENT DOCUMENTS

| | | | |
|---|---|---|---|
| 7,566,884 B2 | 7/2009 | Deguchi et al. | |
| 8,143,593 B2 | 3/2012 | Mirko Milas et al. | |
| 8,178,851 B2 | 5/2012 | Deshmukh et al. | |
| 8,424,144 B2* | 4/2013 | Nanda | A46B 15/0002 15/105 |
| 8,497,487 B2 | 7/2013 | Mirko Miles et al. | |
| 8,698,098 B2 | 4/2014 | Deshmukh et al. | |
| 9,198,502 B2* | 12/2015 | Barnes | A46B 9/04 |
| 2004/0108459 A1 | 6/2004 | Furukawa | G01N 23/2251 250/311 |
| 2006/0129211 A1* | 6/2006 | Canitano | A61N 5/0616 607/89 |
| 2008/0173813 A1* | 7/2008 | Van De Water | G01N 23/04 250/307 |
| 2011/0168876 A1 | 7/2011 | Hsiao | |
| 2011/0180724 A1* | 7/2011 | Terada | H01J 37/185 250/442.11 |
| 2012/0025103 A1 | 2/2012 | Deshmukh et al. | |
| 2012/0138792 A1 | 6/2012 | Danilov et al. | |
| 2012/0212583 A1* | 8/2012 | Yaguchi | G01N 23/2204 348/46 |
| 2012/0225103 A1* | 9/2012 | Theobald | A61K 31/428 424/400 |
| 2013/0329409 A1* | 12/2013 | Windom | F21V 5/04 362/187 |
| 2014/0034829 A1* | 2/2014 | Crozier | H01J 37/226 250/307 |
| 2014/0120746 A1* | 5/2014 | Persion | G02B 6/3817 439/39 |
| 2015/0206703 A1* | 7/2015 | Kobayashi | H01J 37/26 250/311 |
| 2015/0243473 A1* | 8/2015 | Price | H01J 37/20 250/442.11 |
| 2016/0336144 A1* | 11/2016 | Gardiner | H01J 37/26 |

FOREIGN PATENT DOCUMENTS

| | | |
|---|---|---|
| EP | 1503399 | 2/2005 |
| EP | 2419215 | 2/2012 |
| JP | 2006331979 | 12/2006 |
| TW | 201216316 A | 4/2012 |
| TW | 201331624 A | 8/2013 |
| TW | M502242 | 6/2015 |

OTHER PUBLICATIONS

Mehraeen S et al., "A (S)TEM gas cell holder with localized laser heating for in situ experiments." Microsc Microanal Apr. 2013;19(2):470-8. doi: 10.1017/S1431927612014419. Epub Mar. 4, 2013.

Kawamoto N et al., "Transmission electron microscope as an ultimate tool for nanomaterial property studies." Microscopy (Oxf). Feb. 2013;62(1):157-75. doi: 10.1093/jmicro/dfs078. Epub Dec. 7, 2012.

Miller BK et al., "System for in situ UV-visible illumination of environmental transmission electron microscopy samples." Microsc Microanal. Apr. 2013;19(2):461-9. doi: 10.1017/S1431927612014122. Epub Jan. 14, 2013.

Dillon, S.J. et al., "In-Situ TEM in Complex Environments: Photocatalysis" Microscopy and Microanalysis, vol. 18, issue S2, pp. 1072-1073.

Taiwan Intellectual Property Office, "Office Action", dated May 27, 2016.

* cited by examiner

SAMPLE HOLDING DEVICE FOR STUDYING LIGHT-DRIVEN REACTIONS AND SAMPLE ANALYSIS METHOD USING THE SAME

TECHNICAL FIELD

The present disclosure relates to a sample holding device for studying light-driven reactions and a sample analysis method using the same, and more particularly, to a portable sample holding device with high observation reliability that is designed with a detachable light source for real-time replacement and is able to operate without the help of any external driving part.

BACKGROUND

Transmission electron microscope (TEM) is known as a powerful analytical tool for developing and researching materials. With a rapid development of material innovation, the use of TEM is no longer restricted to inspect and analyze samples in static mode, but there are more and more material researches depending on the help of in-situ TEM observations to "see" the real-time progress about the formation or degradation of materials.

Up to now, most sample holding devices that are used for the in-situ TEM studies of light-driven reactions are not able to function independently without the existence of external light sources or power sources, and thereby, the whole task for the experimental preparation can become very cumbersome. In addition, since the external light sources or power sources are generally connected to such sample holding devices by wires, the in-situ studies based on such sample holding devices can be easily affected by ambient mechanical disturbances that are transmitted to the sample holding devices via the wire connections, and thus the analysis stability and resolution are adversely affected. Even for those sample holding devices without the need of external light sources or power sources, they generally can only allow the sample to be irradiated by a fixed light source during the whole analytical operation, resulting in that the variability of the environmental parameters in the in-situ researches of light-driven reactions is restricted.

SUMMARY

In an embodiment, the present disclosure provides a sample holding device for studying light-driven reactions. The sample holding device comprises a main body, a supporting structure, and a light source assembly. The main body is formed with a channel having a first end and a second end that are disposed opposite to each other, while the main body enables a focusing lens to be located on the second end. The supporting structure is located on one end of the main body for sample supporting. The light source assembly is detachably disposed on the other end opposite to the end where the supporting structure is located. The light source assembly emits a light beam into the first end of the channel. The light beam then irradiates the sample which locates on the supporting structure after passing through the focusing lens.

In another embodiment, the present disclosure provides a sample analysis method, which comprises the steps of:

Place a holding part holding a sample to be observed on a carrier of a supporting structure belonging to a sample holding device;

Rotate a rotary shaft for adjusting the tilting of the carrier and the holding part;

Mount the sample holding device on a transmission electron microscope, and then allow an electron beam to irradiate the sample located inside an analytical area of the holding part;

Drive the light source of a light source assembly mounted on the sample holding device for enabling a light beam from the light source to project directly to the analytical area after the light beam is focused by a focusing lens; and Enable an in-situ observation of a specific light-driven reaction.

Further scope of applicability of the present application will become more apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
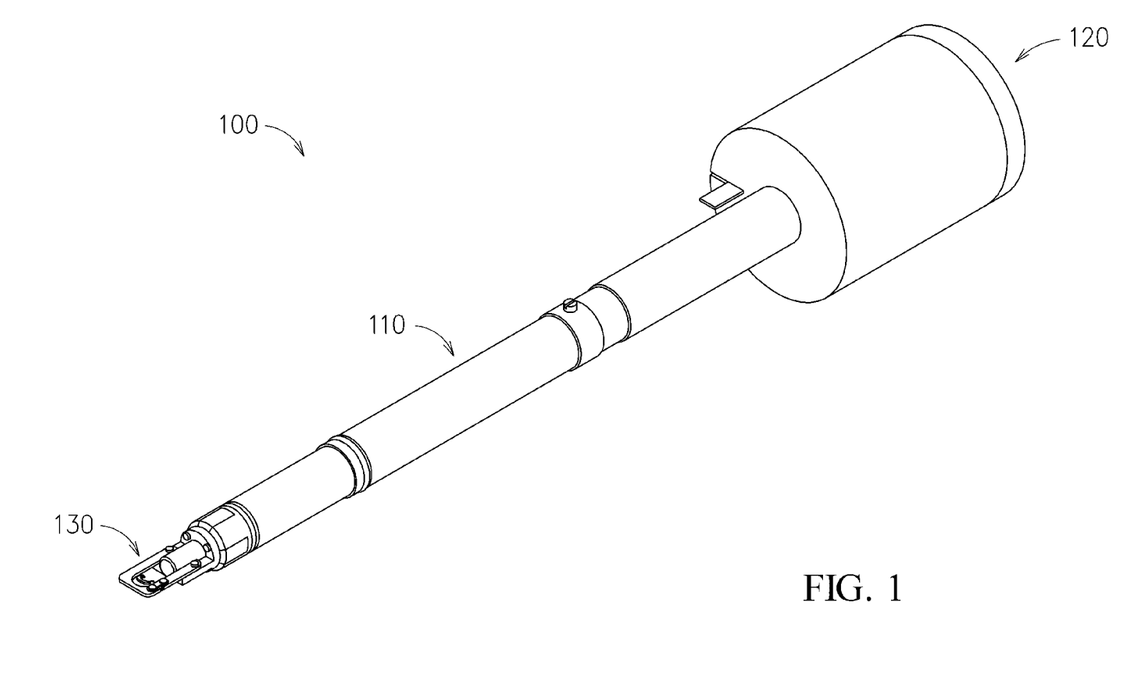
FIG. 1 is a three-dimensional diagram showing a sample holding device according to an embodiment of the present disclosure.
Figure 2:
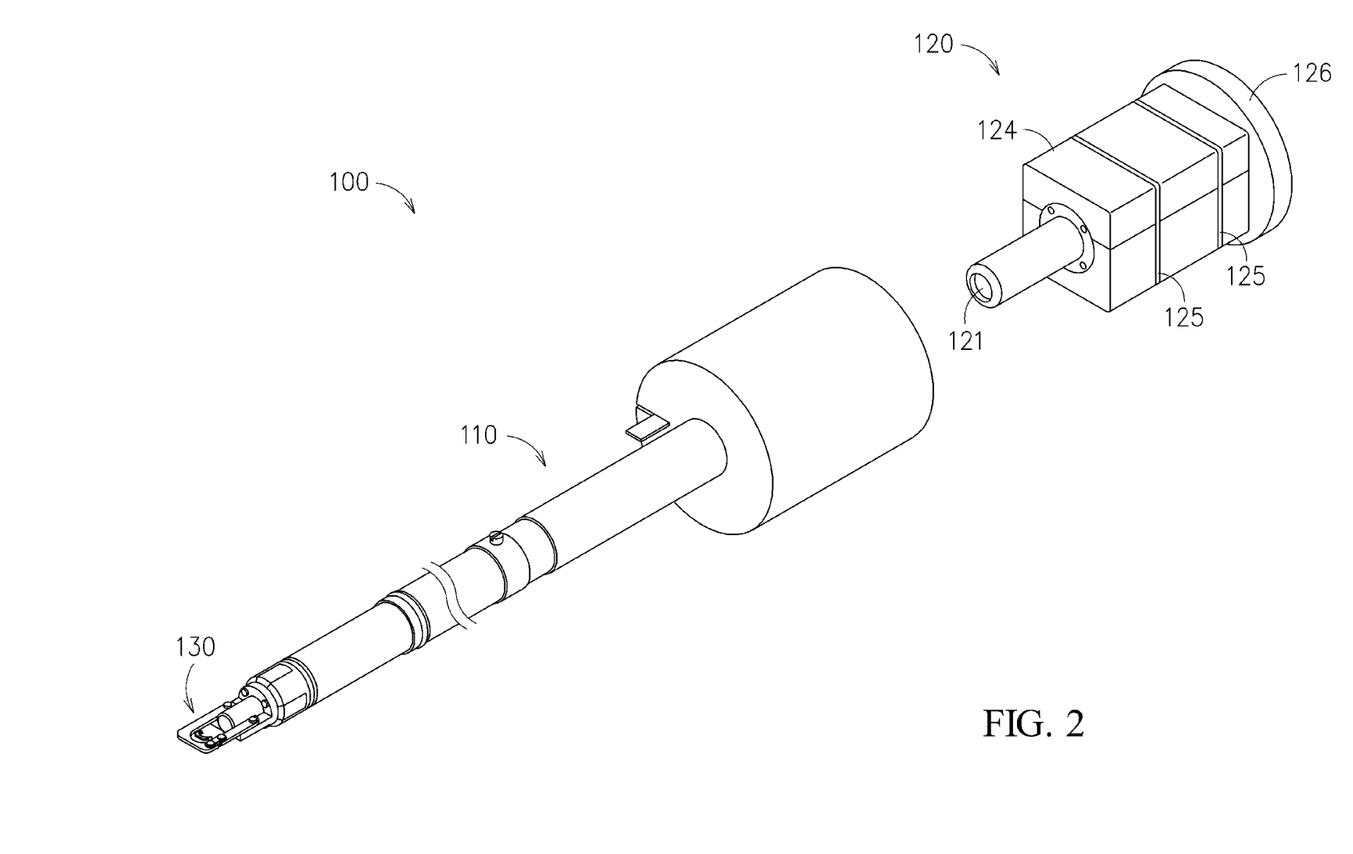
FIG. 2 is a three-dimensional diagram showing the sample holding device of FIG. 1 where its light source assembly is detached from the main body.

Please refer to FIG. 1 and FIG. 2, which are schematic diagrams showing a sample holding device according to an embodiment of the present disclosure, In FIG. 1 and FIG. 2, a sample holding device 100 for studying light-driven reactions is disclosed, which comprises: a main body 110, a light source assembly 120, and a supporting structure 130.

Figures 3, 4:
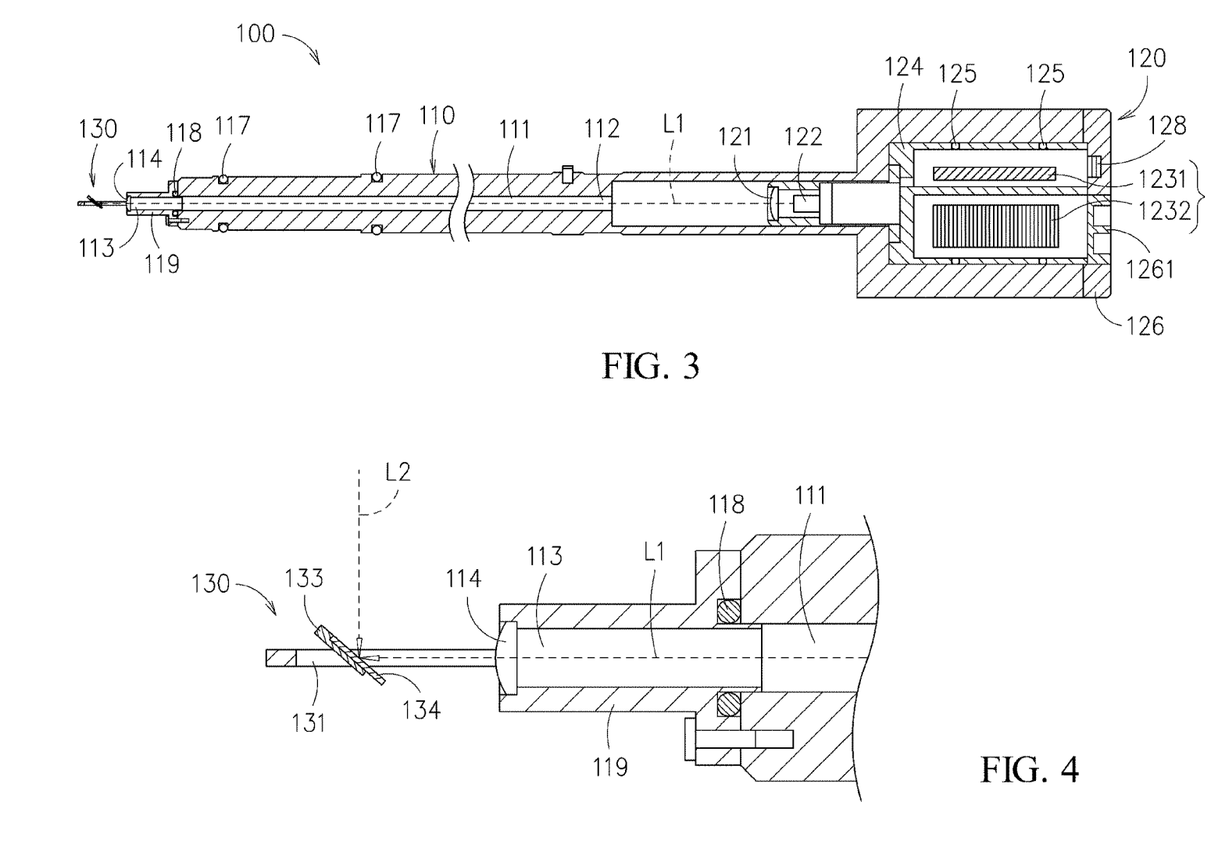
FIG. 3 is a cross sectional view of the sample holding device of FIG. 1.
FIG. 4 is an enlarged cross sectional view of a supporting structure in the sample holding device of FIG. 1.
Figure 5:
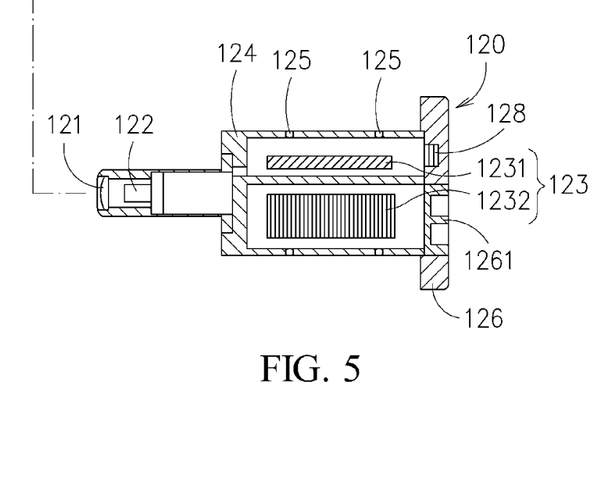
FIG. 5 is a cross sectional view of the sample holding device of FIG. 1 where its light source assembly is detached from the main body.

As shown in FIG. 3, FIG. 4 and FIG. 5, the main body 110 is formed with a channel 111 having a first end 112 and a second end 113 that are disposed opposite to each other, while the main body 110 enables a focusing lens 114 to be located on the second end 113; the light source assembly 120 and the supporting structure 130 are arranged respectively at two opposite ends of the main body 110, i.e. the light source assembly 120 and the supporting structure 130 are arranged at positions corresponding respectively to the first end 112 and the second end 113.

As shown in FIG. 2 to FIG. 6, the light source assembly 120 is detachably disposed on the main body 110. Thereby, the sample holding device 100 for studying light-driven reactions is characterized by its removable light source assembly 120. In this embodiment, the main body 110 is formed with an accommodation space 115 locating at an end where the light source assembly 120 is disposed, and the accommodation space 115 is formed in connection with the channel 111. The accommodation space allows the light source assembly 120 to be embedded therein firmly without being locked. As shown in FIG. 2, the portion of the light source assembly 120 that is to be inset into the main body 110 can be formed as an integration of a cylinder and a block; in accordance with that the accommodation space 115 is formed in a shape conforming to the integration of the cylinder and the block. That is to say, the light source assembly 120 and the accommodation space 115 can be formed into any shape only if the two are conforming to each other. Furthermore, there is a connecting part 119 disposed at the front of the main body 110. The connecting part 119 is used for siting the focusing lens 114 and the supporting structure 130. There are two rubber rings 117 disposed on the periphery of the main body 110, and there is also a rubber ring 118 disposed at the rear of the connecting part 119. The rubber rings 117, 118 are used for preventing the internal vacuum of the TEM mounted with the sample holding device 100 from leakage.

Figure 6:
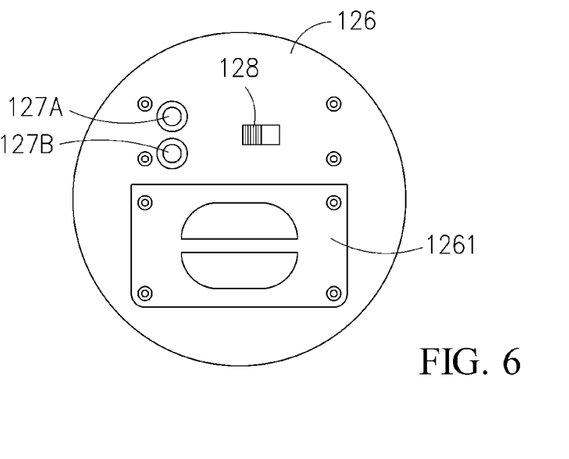
FIG. 6 is a schematic diagram showing an exemplary back panel arrangement for a removable light source assembly used in the sample holding device of FIG. 1.

The light source assembly 120 further comprises: a collimating lens 121, a light source 122, a control unit 123, and a shell 124, provided for housing the collimation lens 121, the light source 122, and the control unit 123. The light source 122 is provided for projecting a light beam L1 toward the collimating lens 121, and the lighting core of the light source 122, for example, a laser diode, a light emitting diode, or an incandescent bulb, can be selected according to the research requirements. The control unit 123 is coupled to the light source 122 and is composed of a driving circuit 1231 and a power source 1232. The driving circuit 1231 that is used for controlling the light source 122 can be further composed of voltage regulators, relays, capacitors, resistors, and a wireless communication unit, in which the communication interface can be selected from the group consisting of: a Bluetooth interface, a ZigBee interface, a WiFi interface, and an infrared interface, by that the light source 122 can be turned on or turned off in a wireless manner. In addition, the power source 1232 can be a disposable battery or a rechargeable battery. It is noted that there can be rubber rings 125 disposed on the outer periphery of the shell 124. With the assistance of the rubber rings 125, the light source assembly 120 can be easily and tightly fitted into the accommodation space 115. Moreover, the shell 124 is further formed with a back panel 126, which is provided for disposing indication lights 127A, 127B and a switch 128. It is noted that the indication lights 127A, 127B are coupling to the driving circuit 1231 for displaying the output status of the light source 122 and the communication status of the wireless communication unit, respectively. The switch 128 is electrically arranged between the driving circuit 1231 and the power source 1232, by that the power from the power source 1232 can be transmitted to the driving circuit 1231 when the switch 128 is ON.

Figure 8:
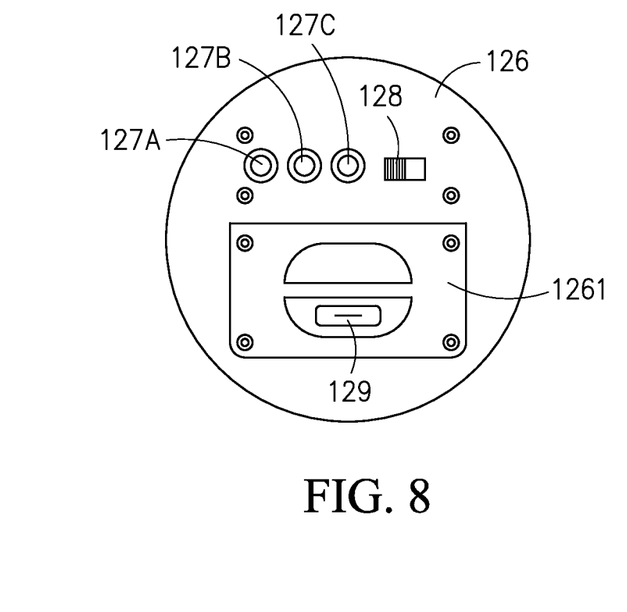
FIG. 8 is a schematic diagram showing another exemplary back panel arrangement for a removable light source assembly used in the sample holding device of FIG. 1.

The amount of the indication light is not restricted to be only two as indicated in the foregoing embodiment and can be determined according to actual requirements. For instance, when the light source is designed with two output levels, it is able to arrange two indication lights to represent these two levels. In such circumstance, as is shown in FIG. 8, three indication lights 127A, 127B, and 127C are used for indicating the low-brightness output, the high-brightness output, and the wireless communicating status, respectively.

In a condition when a disposable battery is used as the power source 1232, it can be replaced when the power supply is insufficient via the detachable battery cover 1261 located on the back panel 126. However, if a rechargeable battery is used as the power source 1232, an electric connection is enabled between the rechargeable battery and a charge socket 129 that is formed on the back panel 126. The charge socket 129 can be electrically connected to an external power source for recharging the power source 1232.

Figure 7:
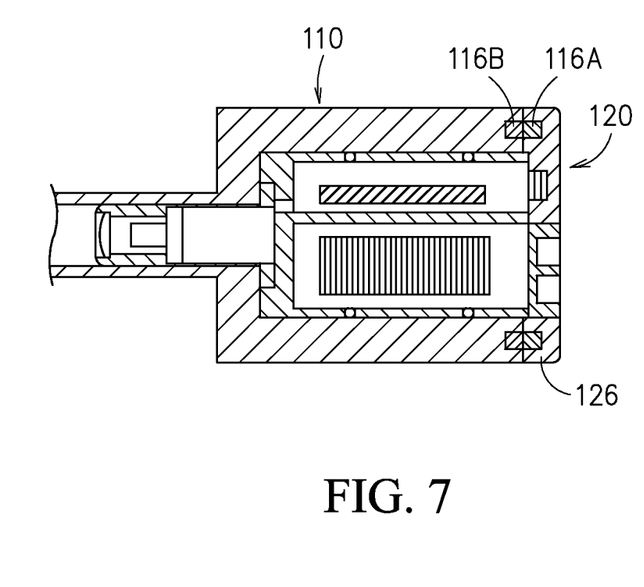
FIG. 7 is a cross section diagram showing the assembly of a main body and a light source assembly according to another embodiment of the present disclosure.

Please refer to FIG. 7, which is a cross section diagram showing the assembly of the main body 110 and the light source assembly 120 according to another embodiment of the present disclosure. The difference between the embodiment of FIG. 7 and the foregoing embodiment is that: the back panel 126 further has a set of magnetic bodies 116A mounted thereon, and the main body 110 also has another set of magnetic bodies 116B mounted thereon. The two set of magnetic bodies 116A and 116B are attractive to each other and their positions are mutually aligned in accordance with the proper combination of the main body 110 and the light source assembly 120.

Figure 9:
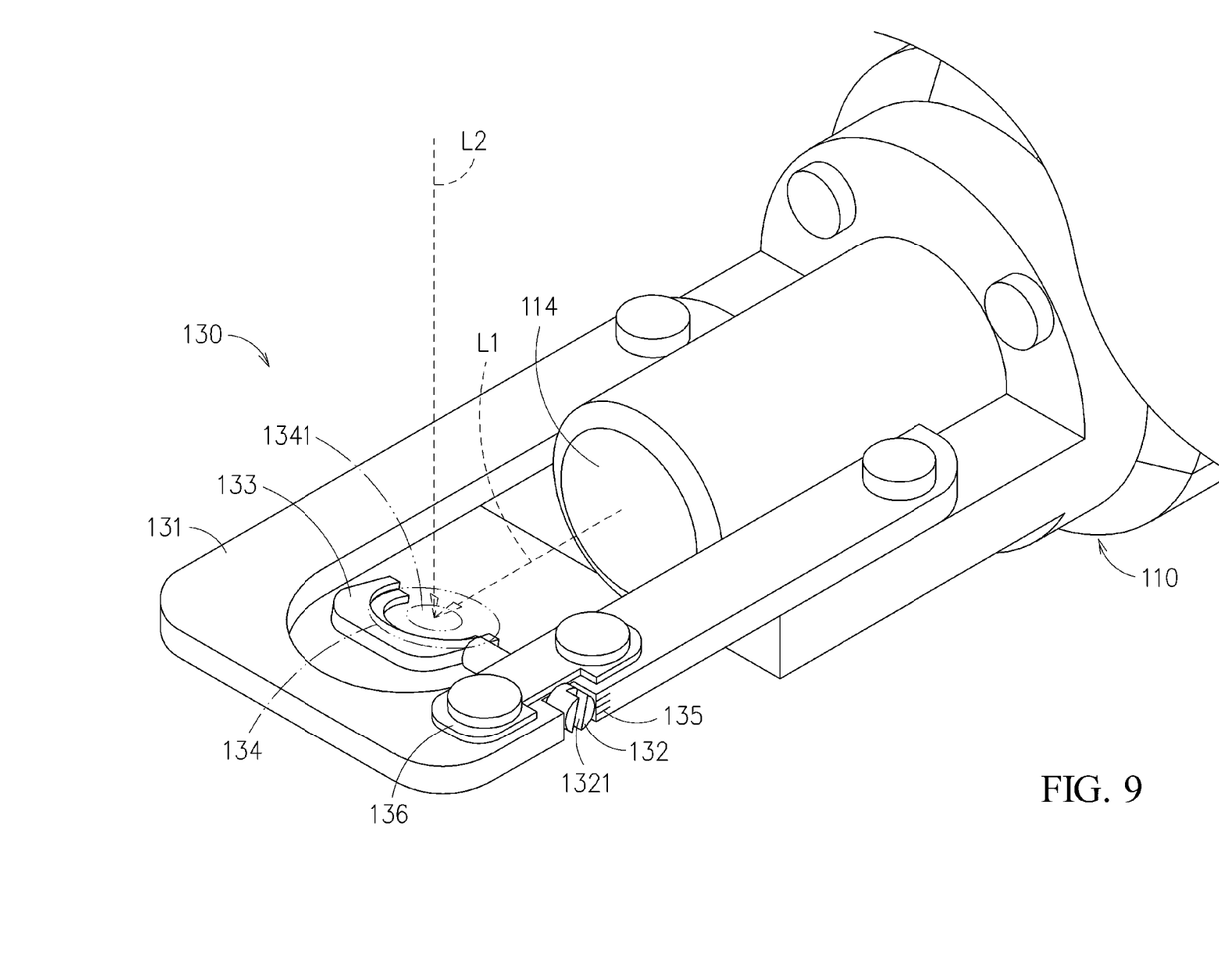
FIG. 9 is a three-dimensional diagram showing a supporting structure used in the sample holding device of FIG. 1.

As shown in FIG. 3, FIG. 4 and FIG. 9, the supporting structure 130 is used for supporting and carrying a sample, which includes a rack 131, a rotary shaft 132, and a carrier 133. The rack 131 is mounted on the main body 110 at a position corresponding to the focusing lens 114 that is disposed on the second end 113 of the channel 111. The rotary shaft 132 is mounted on the rack 131 in a manner that the axis of the rotary shaft 132 is positioned on the same level with the optical axis of the light beam L1, while the configuration allows the axis of the rotary shaft 132 to intercept the optical axis of the light beam L1 by an angle. The carrier 133 is coupled to the rotary shaft 132 for allowing the carrier 133 to be brought along to rotate with the rotary shaft 132. Moreover, the carrier 133 is provided for carrying a holding part 134 that is to be used for holding a sample. The holding part 134 is detachably disposed on the carrier 133, by that when the carrier 133 is being brought along to rotate by the rotary shaft 132, the holding part 134 is being driven to rotate accordingly. In addition, by further forming marks 135 at a side of the rack 131 corresponding to the rotary shaft 132, the tilting angle of the carrier 133 can be identified by the operator; and moreover, by forming a groove 1321 on the outward end of the rotary shaft 132, the rotation of the rotary shaft 132 can be enabled simply by the use of a screw driver. It is noted that the holding part 134 can be formed in any shape, for example, a standard TEM grid or a semi-circular structure with protrusions. The holding part 134 has an analytical area 1341, which possesses a size smaller than the size of the light spot that is the projection of the light beam L1 forming on the holding part 134 after the light beam L1 is focused by the focusing lens 114. In this embodiment, the rack 131 has an adjustable fixing part 136 which is arranged at a position corresponding to the rotary shaft 132 and is provided for exerting an adjustable fixing force on the rotary shaft just sufficiently enough for allowing the rotary shaft 132 to rotate with sufficient freedom while being able to attach itself fixedly on the rack 131. In a summary interpretation of the geometrical concept about the sample supporting of the supporting structure 130, the axis of the rotary shaft 132 intercepts the optical axis of the light beam L1, and the center of the analytical area 1341 of the holding part 134 is located at about the interception of the axis of the rotary shaft 132 and the optical axis of the light beam L1.

Figure 10:
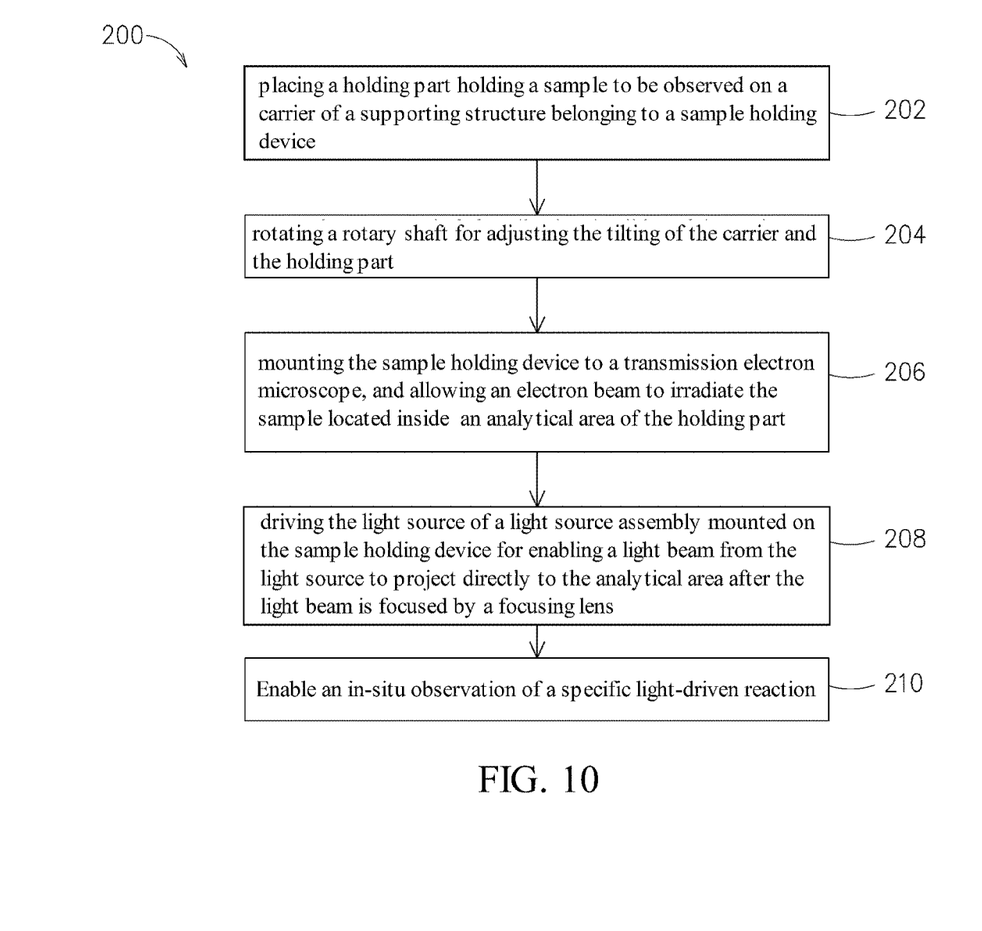
FIG. 10 is a flow chart depicting the steps performed in an in-situ sample analysis method of the present disclosure.

Please refer to FIG. 3, FIG. 4, FIG. 9 and FIG. 10, in which FIG. 10 is a flow chart depicting the steps performed in an in-situ sample analysis method of the present disclosure. In FIG. 10, the method comprises the following steps:

Step 202: Place the holding part 134 holding a sample to be observed on the carrier 133. An analytical area 1341, which can be for example a circular area with 100 μm in radius and positioned at the center of the holding part 134, is pre-defined and marked by geometrical characteristics or a marker/markers;

Step 204: Rotate the rotary shaft 132 for adjusting the tilting of the carrier 133 and the holding part 134, with which the axis of the rotary shaft 132 is positioned on the same level with the optical axis of the light beam L1, so that the axis of the rotary shaft is allowed to intercept the optical axis of the light beam L1 by an angle. The center of the analytical area 1341 of the holding part 134 is located at about the interception of the axis of the rotary shaft 132 and the optical axis of the light beam L1; thereby, the analytical area 1341 will remain inside the projection of the light beam L1 no matter what tilting angle the holding part 134 is tilted to;

Step 206: Mount the sample holding device 100 on a TEM and allow an electron beam L2 to irradiate the sample located inside the analytical area 1341. With the design of the supporting structure 130, the electron beam L2 and the light beam L1 can be projected simultaneously on the sample for in-situ observation, so that in an in-situ study, the observer is able to confirm the sample is actual projected by the light beam L1 simply by confirming the sample is exactly located inside the analytical area 1341;

Step 208: Drive the light source 122 of the light source assembly 120 mounted on the sample holding device 100 for enabling the light beam L1 to emit from the light source 122 and project directly to the analytical area 1341 after the light beam L1 is focused by the focusing lens 114. Operationally, first an operator operates a controller such as a cellular phone or a computer to issue a control signal wirelessly to the wireless communication interface of the light source assembly 120 for turning on the light source 122 into a specific initial output status; then, the light beam L1 that is emitted out of the light source 122 passes through the collimating lens 121, the channel 111, and the focusing lens 114. After being focused by the focusing lens 114, the light beam L1 finally projects to the analytical area 1341 of the holding part 134;

Step 210: Enable the in-situ observation of a specific light-driven reaction, in which the operator is enabled to observe the light-driven reaction on the sample with using the TEM; in the in-situ observation, the output strength/duration of the light source 122 can be controlled either manually or automatically in a wireless manner via a cellular phone or a computer; moreover, during the in-situ observation, the light source assembly 120 can be detached and replaced by another light source assembly possesses a different optical characteristic without having to detach the whole sample holding device 100 from the TEM, so that the step 208 to the step 210 can be repeated multiple times for achieving the in-situ observation of a specific light-driven reaction which is attempted to be driven by various kinds of light sources.

From the above description, it is noted that the sample holding device 100 of the present disclosure is able to overcome the aforesaid conventional shortcomings, i.e. most sample holding devices that are used for the in-situ TEM studies of light-driven reactions are not able to function independently without the existence of external light sources or power sources, and thereby, the whole task for the experimental preparation in the in-situ studies of light-driven reactions can become very cumbersome. In addition, since the external light sources or power sources are generally being connected to such sample holding devices by wires, the in-situ studies based on such sample holding devices can be easily affected by ambient mechanical disturbances that are being transmitted to the sample holding devices through the wire connections.

In addition, the light source assembly 120 in the sample holding device 100 of the present disclosure can be detached from or installed on the main body 110 easily without using any tool, which facilitates the replacement of the light source assemblies that possess different optical characteristics, e.g. wavelength, bandwidth, etc. Moreover, in an in-situ observation, since the accommodation space formed inside the main body 110 for receiving the light source assembly 120 does not connect to the vacuum environment inside the TEM, that further facilitates the detaching/replacing of the light source assembly 120 while the sample holding device 100 is being mounted on a TEM, and thus an in-situ observation of a specific light-driven reaction which is attempt to be driven by various kinds of light sources can be achieved.

In addition, the sample holding device 100 of the present disclosure uses a concentric design. As shown in FIG. 9, regarding to the arrangement of the carrier 133, the holding part 134, the rotary shaft 132, and the optical axis of the light beam L1, the axis of the rotary shaft 132 is positioned on the same level with the optical axis of the light beam L1, while the configuration allows the axis of the rotary shaft to intercept the optical axis of the light beam L1 by an angle; the center of the analytical area 1341 of the holding part 134 is located at about the interception of the axis of the rotary shaft 132 and the optical axis of the light beam L1, thereby, the analytical area 1341 will remain inside the projection of the light beam L1 no matter what tilting angle the holding part 134 is tilted to. Consequently, in an in-situ research, the observer is able to make sure the observed object is actually projected by the light beam simply by just looking for a sample that is exactly located inside the analytical area 1341.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A sample holding device for studying light-driven reactions with an electron microscope, comprising:
  a main body, comprising:
    a channel;
    a focusing lens, located in the channel; and
    an accommodation space, concentric with the channel;
  a sample supporting structure, located on one end of the main body; and
  a light source assembly, detachably disposed in the accommodation space on the other end of the main body opposite to the sample supporting structure, conforming to the accommodation space to emit a light beam into the channel and through the focusing lens to irradiate a sample located on the sample supporting structure,
  wherein said sample supporting structure is configured to be inserted within said electron microscope.

2. The sample holding device of claim 1, wherein the light source assembly comprises:
  a collimating lens;
  a light source, for projecting a light beam toward the collimating lens;
  a control unit, coupled to the light source; and
  a shell, for housing the collimating lens, the light source, and the control unit.

3. The sample holding device of claim 2, wherein the control unit further comprises a driving circuit and a power source; the shell is formed with a back panel, and the back panel further comprises:
  at least one indication light, each coupled to the control unit; and
  a switch, coupled to the driving circuit and the power source.

4. The sample holding device of claim 3, wherein the power source is a rechargeable battery, and the back panel is formed with a charge socket that is coupled to the rechargeable battery.

5. The sample holding device of claim 3, wherein the power source is a disposable battery.

6. The sample holding device of claim 3, wherein the driving circuit includes at least one wireless communication unit.

7. The sample holding device of claim 2, wherein the shell further has a set of magnetic bodies mounted thereon, the main body also has another set of magnetic bodies mounted thereon, and the two sets of magnetic bodies are attracted to each other for strengthening the combination of the shell and the main body.

8. The sample holding device of claim 1, wherein the sample supporting structure further comprises:
  a rack, mounted on the main body;
  a rotary shaft, mounted on the rack in a manner that the axis of the rotary shaft is positioned on the same level with the optical axis of the light beam, while the configuration allows the axis of the rotary shaft to intercept the optical axis of the light beam by an angle; and
  a carrier, used for carrying the sample, is coupled to the rotary shaft for allowing the carrier to be brought along to rotate with the rotary shaft.

9. The sample holding device of claim 8, wherein the sample is disposed on a holding part while the holding part is detachably disposed on the carrier.

10. The sample holding device of claim 9, wherein the holding part is formed with an analytical area in a manner that the center of the analytical area is located at about the interception of the axis of the rotary shaft and the optical axis of the light beam.

11. The sample holding device of claim 1, wherein the light source assembly is substantially complementary to the accommodation space.

12. The sample holding device of claim 3, wherein the back panel abuts the main body.

* * * * *